United States Patent [19]

Stüber

[11] Patent Number: 4,713,369

[45] Date of Patent: Dec. 15, 1987

[54] OLIGOPEPTIDYLARGININOL DERIVATIVES AND THEIR HOMOLOGS, A PROCESS FOR THEIR PREPARATION, THEIR USE AND AGENTS CONTAINING THEM

[75] Inventor: Werner Stüber, Lahntal, Fed. Rep. of Germany

[73] Assignee: Behringwerke Aktiengesellschaft, Fed. Rep. of Germany

[21] Appl. No.: 829,482

[22] Filed: Feb. 14, 1986

[30] Foreign Application Priority Data

Feb. 18, 1985 [DE] Fed. Rep. of Germany ....... 3505555

[51] Int. Cl.$^4$ .................. A61K 37/43; C07K 5/08; C07C 103/20
[52] U.S. Cl. .................. 514/18; 530/331; 564/157; 564/158; 514/616
[58] Field of Search ............ 514/18, 616; 530/331; 564/157, 158

[56] References Cited

PUBLICATIONS

Synthetic Organic Chemistry, Ch. 14, (1953), 480–481.
Mattson et al., Folia Haematol, 109, 43–51, 1982.
Muramatu et al., Biochim. Biophys. Acta 268, 221–224, 1972.
Koltai et al., J. Labelled Compds. 19, 7–11, 1982.
Borin et al., Hoppe–Seyler's Z. Physiol. Chem. 362, 1435–1445, 1981.
Boissonas et al., Helv. Chim. Acta, 16, 1875, 1958.
Moroder et al., Hopp.–Seyler's Z. Physiol. Chem. 357, 1651–1653 (1976).

*Primary Examiner*—Delbert R. Phillips
*Attorney, Agent, or Firm*—Finnegan, Henderson, Farabow, Garrett & Dunner

[57] ABSTRACT

The invention relates to new peptidylargininol derivatives and their homologs of the general formula

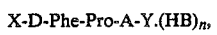

$$X\text{-D-Phe-Pro-A-Y.}(HB)_n,$$

X being a hydrogen atom or a known protective group customary in peptide chemistry,
D-Phe being D-phenylalanine,
Pro being L-proline,
A being a ω-guanidiano-β-aminoalkanol residue of the formula —NHCH $(CH_2)_m$NHC(NH)NH$_2$CH$_2$O, with m being 2 to 5, preferably an argininol residue or a homoargininol residue,
Y being a hydrogen atom or an ester-forming group,
B being an acid residue, and
n being 0, 1 or 2, and to a process for the preparation of these compounds, to pharmaceutical agents containing these compounds, and to the use of these agents as thrombin inhibitors.

8 Claims, No Drawings

OLIGOPEPTIDYLARGININOL DERIVATIVES AND THEIR HOMOLOGS, A PROCESS FOR THEIR PREPARATION, THEIR USE AND AGENTS CONTAINING THEM

The invention relates to new oligopeptidylargininol derivatives and their homologs, to the synthesis of these compounds, to their use and to pharmaceutical agents which contain the new compounds, which are highly active thrombin inhibitors.

It is known that under a whole range of pathophysiological conditions there is formation of thrombin/antithromin (AT) III complexes and thus consumption of the protease inhibitor AT III, the most important thrombin inhibitor in human plasma. A decrease in AT III leads to a high risk of thrombosis, as is also known from, inter alia, cases of inborn AT III deficiency. Reductions to values below 75% of normal result in thromboembolic complications. Nowadays inborn and acquired AT III deficiency states are treated by administration of AT III, which is obtained from the blood plasma of volunteer donors. Since blood plasma is available only in restricted amounts, there are limits to the clinical use of AT III. From this viewpoint, it is desirable to seek synthetic inhibitors which are able, in a manner comparable to that of natural AT III, to close the enzyme cavity of thrombin or to block chemically the active serine residue of the protease thrombin. On the basis of the specificity of thrombin, arginine derivatives come under consideration for this, because they fit well into the enzyme cavity of thrombin, in particular those which have as the reactive group aldehydes or chloromethyl ketones.

It is known that peptides based on Phe-Pro-Arg prove to be favorable, especially when the N-terminal amino acid is in the D-form (C. Mattson, E. Eriksson and S. Nilsson, Folia Haematol. 109, 43–51, 1982). Inhibitors acting competitively which may be mentioned in this connection are: D-Phe-Pro-Arg isopropyl ester and D-Phe-Pro-Arg-4-methylpiperidine.

It is also known that a potentiation of the inhibitory action can be brought about by derivatization at the C-terminal end in such a manner that there is now reaction with the "active" serine or the activating histidine. Argininals or chloromethyl ketones of arginine have proved to be particularly effective for this. At the same time, argininals should be able to undergo hemiacetal bonding with the serine hydroxyl. In contrast, chloromethyl ketones should bring about $N^{im}$-alkylations. With both inhibitor models N-terminal D-Phe-Pro brought about high affinity to thrombin.

A number of other compounds which act as thrombin inhibitors and are structurally related to arginine and show variations at the N- and C-terminal ends are known. An example which may be mentioned is p-carboxyethylphenyl ε-guanidinocaproate (M. Muramatu and S. Fujii, Biochim. Biophys. Acta 268, 221–224, 1972).

It has now been found, surprisingly, that the form of the peptide D-Phe-Pro-Arg which is completely reduced at the C-terminal end, ie. D-Phe-Pro-Argininol, brought about a potent inhibition of thrombin.

Thus the invention relates to new substances which are able to inhibit thrombin and have the following structure:

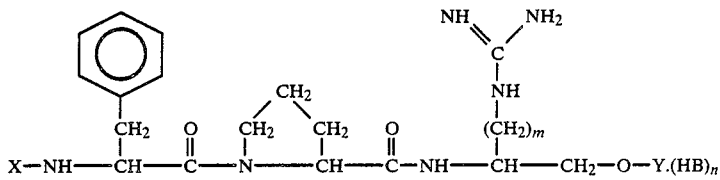

corresponding to the method of representation

X-D-Phe-Pro-A-Y (HB)$_{n'}$ in which
X is a hydrogen atom or a protective group customary in peptide chemistry, preferably BOC or Z,
D-Phe is D-phenylalanine,
Pro is L-proline,
A is an ωguanidino-β-aminoalkanol residue (argininol and homologs of the formula —NHCH(CH$_2$)$_m$NHC(NH)NH$_2$—CH$_2$O—, m being 2 to 5, preferably 3 or 4,
Y is a hydrogen atom or
Y is an ester-forming group of the structure OC—R, with R=H or an aliphatic radical having up to 4 carbon atoms, or

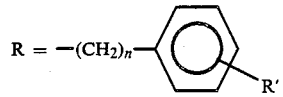

R' being H, CH$_3$, OCH$_3$ or NO$_2$, and n being 0, 1 or 2, or
Y is an ester-forming group of the structure —SO$_2$—R, with R=OH, an araliphatic or aromatic radical of the structure

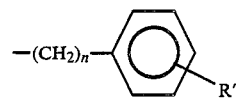

R' being H, CH$_3$ or OCH$_3$, and n being 0, 1 or 2,
B is an acid residue, and
n is 0, 1 or 2.

The compounds according to the invention are prepared by methods customary in peptide chemistry, namely either by fragment condensation or by stepwise synthesis, protective groups which have been temporarily introduced being eliminated and, where appropriate, the resulting compounds being converted into their physiologically tolerated salts.

First, argininol, which is also designated ArgCH$_2$OH in the following text, or its homolog is synthesized as the parent substance. For this purpose, for example the method known from the literature, that of E. Koltai et al. (E. Koltai, B. Horvath and D. Banfi, J. Labelled Compds. 19, 7-11, 1982), is used for the preparation of L-$N^G$-nitroargininol hydrobromide, but preferably dispensing with $N^G$-blocking.

Carbon atom 2 of argininol, or carbon atom 2 of the argininol homologs, is chiral, for which reason the D- and L-forms are possible.

The L-form is preferably used.

Argininol and homoargininol and their homologs can be prepared by reduction of suitable derivatives using complex hydrides. Suitable derivatives are alkyl esters having 1-6 carbon atoms; the methyl esters are particularly suitable.

In order to guarantee good solubility and to avert the formation of byproducts during the reaction, use is made of the protective groups customary in peptide chemistry. For example, the protective groups which can be used for the primary amino group are the triphenylmethyl (Trt), carbobenzoxy (Z) or butyloxycarbonyl (Boc) groups. The Trt group is preferably used. The reducing agents used are the compounds known from the state of the art; lithium aluminum hydride in absolute tetrahydrofuran, or sodium borohydride with calcium chloride in ethanol is preferably used, and lithium aluminum hydride is particularly preferred.

The reductions are always carried out with an excess of complex hydrides. The purity of the products is investigated by thin-layer chromatography. The hydroxyl groups can be detected by infra-red spectroscopy using the C—O vibration at 1040 $cm^{-1}$. In the case of Trt-Arg $CH_2OH$ compound, the lack of carbonyl bands in the infra-red spectrum demonstrates that reduction is complete.

The N-protected argininols or homoargininols and homologs can be converted, using acid chlorides or anhydrides by known methods, into the corresponding esters, acid chlorides preferably being used. The N-protective groups are eliminated from free or esterified argininols or homoargininols or the homolog by known methods.

The free or esterified argininols or homoargininols or their homologs are reacted, by procedures customary in peptide chemistry, with the dipeptide D-Phe-Pro which is preferably protected at the N-terminal end with Boc or Z. Active ester couplings are suitable and preferred for this purpose.

During the course of the synthesis of the compounds according to the invention, X-D-Phe-Pro-A-Y corresponding to the abovementioned structure, it is, of course, possible to use the protective groups customary in peptide chemistry. This means that the alcohol group of argininol or homoargininol or their homologs can, for example, be etherified, and the guanidino group can, for example, be in the form of a nitro compound. The dipeptide derivative can either be incorporated as such, or the incorporation can be carried out steowise by incorporation of single, protected, activated amino acids. Suitable N-terminal protective groups are the protective groups which are customary in peptide chemistry, preferably those which are physiologically tolerated, for example butyloxycarbonyl (Boc), carbobenzoxy (Z), fluorenylmethyloxycarbonyl (Fmoc) and biphenylylpropyloxycarbonyl (Bpoc), preferably Boc or Z.

The protective groups are eliminated in a known manner using the reagents customarily used for this in peptide chemistry.

The N-protective group which is preferably used is the Boc group, this being preferably eliminated with 1.2 molar hydrogen chloride in glacial acetic acid or trifluoroacetic acid.

Surprisingly, the compounds according to the invention exhibited a potent inhibitory action on thrombin. The anticoagulant action of the D-phenylalanyl-L-propyl-Largininol derivatives and the corresponding homoargininol argininol derivatives is extremely pronounced, and the inhibitory action of the D-phenylalanyl-L-prolyl-L-argininol is especially strong. It is especially surprising that the new dipeptidylargininol derivatives are particularly active as thrombin inhibitors because this effect is in marked contrast to results obtained with the spermatozoal endoprotease acrosin (G. Borin, G. Chessa, G. Cavaggion, F. Marchiori and W. Müller-Esterl, Hoppe-Seyler's Z. Physiol. Chem. 362, 1435-1445, 1981). These authors specifically prepared Boc-Leu-Leu-argininal . acetic acid . $H_2O$ and found it to be a very active inhibitor. The corresponding argininol derivative, which was likewise prepared in this connection, is described as being completely inactive in the inhibition test. Thus, according to this, it was by no means to be expected that the arginine derivatives of the invention would be unusually active thrombin inhibitors.

The compounds according to the invention are suitable as substitutes for the naturally occurring protease inhibitors, especially for antithrombin III which, as mentioned in the introduction, is obtained from the blood of donors, and, merely for this reason, is available only in limited amounts. At the same time, the inhibitory action of the compounds according to the invention is more specific than that of other known inhibitors, for example that of 4-carboxyethylphenyl $\epsilon$-guanidinocaproate.

The substances according to the invention, and their physiologically tolerated salts, can be used as active components in agents with which AT III deficiency can be abolished and thus the risk of thrombosis eliminated or, at the least, greatly reduced. These agents can additionally contain physiologically acceptable vehicles or other auxiliaries. In the case of parenteral administration, it is also possible to use, for example, solubilizers, emulsifiers and the like, with the aid of which the substances according to the invention are brought into solution, suspension or emulsion. Suitable solvents are: water, physiological saline solutions or alcohols, for example ethanol, propanol or glycerol, as well as sugar solutions, such as glucose or mannitol solutions, or even a mixture of various solvents, but a physiological saline solution is preferably used. The customary pharmaceutical formulations are suitable for oral administrations.

Abbreviations $N^G$—primary amino group of the guanidino group
Boc—tert.-butoxycarbonyl
Trt—triphenylmethyl
Z—benzyloxycarbonyl (=carbobenzoxy)
kim—inhibition constant
N—nitrogen atom of the imidazole ring of histidine
min—minutes
TLC—thin-layer chromatography
$R_F$—retention factor
C/T—chloro/4,4-bis(dimethylamino)diphenylmethane test
UV—ultraviolet visualization at 254 nm
DMF—dimethylformamide

EXAMPLES

Mobile phases for thin-layer chromatography / silica gel chromatography:

| | |
|---|---|
| A: butanol/glacial acetic acid/water | 3:1:1 |
| B: chloroform/methanol/glacial acetic acid | 50:10:2.5 |
| C: chloroform/methanol/glacial acetic acid | 50:10:5 |
| D: chloroform/methanol/glacial acetic acid | 50:20:5 |
| E: chloroform/methanol/glacial acetic acid water | 20:10:2:1 |

Example 1

Step 1:

The methyl ester of tritylarginine hydrochloride was prepared according to the literature (R. A. Boissonas, St. Guttmann, R. L. Huguenin, R. A. Jaquenoud and E. Sandrin, Helv. Chim. Acta, 16, 1875, 1958) and reduced as described in step 2.

Step 2: Tritylargininol hydrochloride (Trt-Arg $CH_2OH.HCl$)

4.2 g of lithium aluminum hydride were suspended in 150 ml of absolute tetrahydrofuran and cooled to 0° C. in an ice bath. 9.3 g of the methyl ester of tritylarginine hydrochloride, which were dissolved in 50 ml of absolute tetrahydrofuran, were slowly added dropwise to this suspension. The mixture was stirred at 0° C. for 30 min and then heated to 40°-45° C. After 30 min, the excess lithium aluminum hydride was decomposed with ice-water. Insolubles were removed by filtration, and the tetrahydrofuran was substantially removed by evaporation. The residue was neutralised with 0.1 N hydrochloric acid, taken up in n-butanol/ethyl acetate (1:1 parts by volume) and the solution was washed with water. After removal of the organic solvent by evaporation, tritylargininol hydrochloride was obtained in the form of a foam.

Yield: 6.9 g (74.2%),

Purity check: TLC $R_F=0.19$ (B) C/T, ninhydrin, Sakaguchi and UV positive 2,4-dinitrophenylhydrazine negative.

Step 3: Argininol ditrifluoroacetate (Arg $CH_2OH$ . 2 $CF_3COOH$)

1 g of tritylargininol hydrochloride was added to 80 ml of a mixture of trifluoroacetic acid/water (1:1 parts by volume) at 0° C., and the mixture was stirred for 15 min. During this a pale yellow coloration and a white precipitate appeared. The mixture was filtered with suction through a sintered glass filter funnel, and the filtrate was evaporated in vacuo. The residue was taken up in water, and the solution was extracted three times with ethyl acetate. The aqueous phase was freeze-dried.

Yield: 950 mg (98%),

Purity check: TLC $R_F=0.1$ (A) C/T, ninhydrin, Sakaguchi positive UV, 2,4-dinitrophenylhydrazine negative.

Step 4

870 mg of Boc-D-Phe-Pro and 370 mg of hydroxybenzotriazole were dissolved in 10 ml of dimethylformamide and, at 0° C., 500 mg of dicyclohexylcarbodiimide were added. After 30 min, 930 mg of argininol ×2 $CF_3COOH$ and 500 μl of N-methylmorpholine were added. The reaction mixture was stirred overnight, the precipitated dicyclohexylurea was filtered off, and the solvent was removed by evaporation in vacuo. The residue was triturated with 100 ml of ethyl acetate, and the precipitate resulting from this was removed by centrifugation. The ethyl acetate solution was separated off, and the solvent was removed by evaporation in vacuo. The oily residue was dissolved in a little ethanol, and the product was crystallized by dropwise addition to diethyl ether. The crystals were filtered off and dried under high vacuum.

Yield: 1.020 mg (68.7%),

Purity check: TCL $R_F=0.23$ (C)

$R_F=0.50$ (D) C/T, UV, ninhydrin, Sakaguchi positive 2,4-dinitrophenylhydrazine negative.

Step 5:

D-Phe-Pro-Arg-$CH_2OH \times 2CF_3COOH$ 930 mg of Boc-D-Phe-Pro-Arg-$CH_2OH \times CF_3COOH$ were stirred with 0.5 ml of anisole and 3 ml of ice-cold trifluoroacetic acid for 10 min. The solution was added dropwise to diethyl ether to crystallise the product. The crystals were collected and dried under high vacuum.

Yield: 818 mg (86%)

Purity check: TLC $R_F=0.31$ (A)

Thin-layer electrophoresis, pyridine acetate buffer, pH 5.2 on cellulose plates: one spot C/T, ninhydrin, UV, Sakaguchi positive 2,4-dinitrophenylhydrazine negative Amino acid analysis: Phe 1.00, Pro 1.06, Arg 0.04, purity 98%.

Example 2

Step 1: Methyl ester of Z-arginine hydrochloride 5.22 g of the methyl ester of arginine hydrochloride were dissolved in dimethylformamide, and 6.83 ml of ethyldiisopropylamine were added, followed by 6.8 g of benzyl chloroformate, dropwise at 0° C. The reaction mixture was then stirred at 40° C. for three hours and at room temperature overnight. The solvent was removed by evaporation in vacuo, the residue was taken up in water, and the solution was extracted with ethyl acetate. The aqueous phase was treated with n-butanol/ethyl acetate (1:1 parts by volume) to extract the product. The organic phase was washed with saturated sodium chloride solution, and the solvent was removed by evaporation in vacuo. A concentrated solution of the residue in methanol was prepared, and precipitation was carried out by addition of this dropwise to ethyl acetate/diethyl ether (1:1 parts by volume).

Yield: 5.8 g (81%)

Purity check: TLC $R_F=0.37$ (B)

C/T, Sakaguchi, UV positive

Ninhydrin negative.

Step 2: Z-argininol hydrochloride (Z-Arq-$CH_2OH \times HCl$)

5.8 g of the methyl ester of Z-arginine hydrochloride were dissolved in 200 ml of ethanol, and 11.8 g of calcium chloride dihydrate were added. 4 g of sodium borohydride were added to this mixture. Then it was heated to 40° C., and the course of the reaction was followed by thin-layer chromatography. It was necessary, where appropriate, to add additional sodium borohydride until starting material was no longer detectable. Insolubles were then removed by filtration, and the residue was washed with ethanol. 30% by volume of water was added to the filtrate, and the precipitate which had separated out was removed by filtration. The solvent was removed by evaporation in vacuo, the residue was taken up in water, and the product was extracted by repeated shaking with butanol/ethyl acetate (2:1 parts by volume). After removal of the solvent by evaporation, the residue was purified on a silica gel column (400 g of silica gel, particle size 40-63 μm, mobile phase E). The combined fractions were further purified by a gel filtration step (sephadex LH 20, mobile phase methanol). After removal of the solvent by evaporation, an oily product was obtained.

Yield: 4 g (72.6%),

Purity check: TLC $R_F=0.46$ (E) C/T, UV, Sakaguchi positive Ninhydrin, 2,4-dinitrophenylhydrazine negative.

Step 3: H-argininol dihydrochloride (H-Arg-CH$_2$OH×2 HCl)

2 g of Z-argininol hydrochloride were hydrogenated in methanol as the solvent and in the presence of palladium/active charcoal. The pH was maintained at 4 using 0.1 N hydrochloric acid. After uptake of hydrogen was complete, the palladium/active charcoal was removed by filtration, and the solvent was removed by evaporation in vacuo.

Yield: 1.36 g (quantitative),

Purity check: TLC $R_F=0.1$ (A) C/T, ninhydrin, Sakaguchi positive 2,4-dinitrophenylhydrazine, UV negative Step 4

870 mg of Boc-D-Phe-Pro and 370 mg of hydroxybenzotriazole were dissolved in 10 ml of dimethylformamide and, at 0° C., 500 mg of dicyclohexylcarbodiimide were added. After 30 min, 766 mg of argininol×2 HCl and 500 μl of N-methylmorpholine were added. The reaction mixture was stirred overnight, the precipitated dicyclohexylurea was removed by filtration, and the solvent was removed by evaporation in vacuo. The residue was triturated with 100 ml of ethyl acetate, and the precipitate which formed during this was removed by centrifugation. The ethyl acetate solution was separated off, and the solvent was removed by evaporation in vacuo. The oily residue was dissolved in a little ethanol, and the product was crystallized by dropwise addition to diethyl ether. The crystals were removed by filtration and dried under high vacuum.

Yield: 1.050 mg (70.72%)

Purity check: TLC $R_F=0.23$ (C) $R_F=0.50$ (D) C/T, UV, ninhydrin, Sakaguchi positive 2,4-dinitrophenylhydrazine negative.

Step 5 D-Phe-Pro-Arg-CH$_2$OH×2CF$_3$COOH 900 mg of Boc-D-Phe-Pro-Arg-CH$_2$OH×HCl were stirred with 0.5 ml of anisole and 3 ml of ice-cold trifluoroacetic acid for 10 min. The solution was added dropwise to diethyl ether to crystallize the product. The crystals were collected and dried under high vacuum.

Yield: 789 mg (85%),

Purity check: TLC $R_F=0.31$ (A)

Thin-layer electrophoresis, pyridine acetate buffer, pH 5.2 on cellulose plates: one spot C/T, ninhydrin, UV, Sakaguchi positive, 2,4-dinitrophenylhydrazine negative Amino acid analysis: Phe 1.00, Pro 1.04, Arg 0.03, purity 97%.

Example 3

Step 1: Boc-argininol 4-nitrobenzoate hydrochloride

Boc-argininol hydrochloride was prepared by reduction of the methyl ester of Boc-arginine hydrochloride in analogy to the Z-compound (Example 2). The introduction of the Boc group was carried out with di-tert.-butyl pyrocarbonate (L. Moroder, A. Hallett, E. Wünsch, 0. Keller and G. Wersin, Hoppe-Seyler's Z. Physiol. Chem. 357, 1651-1653 (1976)).

500 mg of Boc-Arg-CH$_2$OH were dissolved or suspended in 3 ml of pyridine and, at 0° C., 2 g of 4-nitrobenzoyl chloride were added in portions. The mixture was stirred at room temperature for one hour and at 40° C. for 30 min, this resulting in a clear solution. The mixture was crystallised by dropwise addition to ether, and the crystals were filtered and washed with ether. The residue was dissolved in methanol, insolubles were removed by filtration, and the product was precipitated with ether. A yellow oil was obtained and, for further purification, was chromatographed on silica gel (100 g, 40-63 μm particle size, eluting agent E). The fractions were combined, the solvent was removed by evaporation, and rechromatography was carried out on sephadex LH 20 (methanol).

Yield: 450 mg (77.6%)

Purity check: TLC $R_F=0.56$ (C) C/T, UV, ninhydrin, Sakaguchi positive

Step 2: H-argininol 4-nitrobenzoate hydrochloride 430 mg of Boc-argininol 4-nitrobenzoate were stirred with 10 ml of 1.2 N HCl/glacial acetic acid for 25 min with exclusion of moisture. The eliminating reagent was removed by evaporation in vacuo, and evaporation with toluene was carried out several times to drive off adherent traces of acid. The residue was dissolved in the minimum volume of n-butanol, and the product was crystallized by dropwise addition to diethyl ether.

The mass of crystals was removed by centrifugation, washed with ether and dried.

Yield: 250 mg (67.6%)

Purity check: TLC $R_f=0.44$ (A) T, ninhydrin, Sakaguchi positive

Step 3: Boc-D-Phe-Pro-argininol 4-nitrobenzoate hydrochloride 253 mg of Boc-D-Phe-Pro were dissolved together with 107 mg of hydroxybenzotriazol in DMF and, at 0° C., were preactivated with 154 mg of dicyclohexylcarbodiimide for 30 min. 240 mg of argininol-4-nitrobenzoate dihydrochloride and 150 μl of N-methylmorpholine were added to this mixture. The reaction was allowed to run overnight, and the solvent was removed by evaporation in vacuo and the oily residue was taken up in n-butanol/ethyl acetate (1:1 parts by volume). The organic phase was extracted three times with water and was evaporated in a rotary evaporator. A concentrated solution of the crude product in butanol was prepared, and crystallization was carried out by dropwise addition to diethyl ether. The crystals were collected, washed with diethyl ether and dried.

Yield: 370 mg (75.6%)

Purity check: TLC $R_F=0.45$ (B) C/T, UV, ninhydrin, Sakaguchi positive

Step 4: D-Phe-Pro-argininol-4-nitrobenzoate dihydrochloride 350 mg of Boc-D-Phe-Pro-argininol 4-nitrobenzoate dihydrochloride were stirred with 5 ml of 1.2 N HCl/glacial acetic acid for 25 min to eliminate the nitrogen protective group. The eliminating agent was removed by evaporation in vacuo, and the residue was evaporated twice with toluene in a rotary evaporator to remove traces of acid. The oily residue was dissolved in butanol and crystallized by dropwise addition to diethyl ether. The crystals were removed by centrifugation, washed with diethyl ether and dried under high vacuum.

Yield: 290 mg (91.2%)

Purity check: TLC $R_F=0.5$ (E)

$R_F=0.43$ (A) C/T, ninhydrin, UV, Sakaguchi positive

Example 4

Testing of the inhibitory action against human α-thrombin

D-Phe-Pro-argininol ditrifluoroacetate was tested in comparison with 4-carboxyethylphenyl ε-guanidinocaproate (Foy).

Test procedure: 700 μl of tris buffer, pH 8.2, are incubated with 100 μl of human α-thrombin (0.28 UI) and 100 μl of inhibitor solution at 37° C. for 5 min. After addition of 100 μl of Tos-Gly-Pip-Arg paranitroanilide (c×3 mMol/l), the extinction at 405 nm is measured.

50% inhibition was reached in the case of D-Phe-Pro-argininol ditrifluoroacetate at a final concentration of 0.15±0.01 μmol/liter.

In the case of 4-carboxyethylphenyl ε-guanidinocaproate, this figure was at a final concentration of 3.65±0.05 μmol/liter.

The following figures were obtained for the inhibitory action against plasmin and F Xa in an analogous procedure, the final concentration of D-Phe-Pro-argininol ditrifluoroacetate and of 4-carboxyethylphenylε-guanidinocaproate being 0.6 mmol/l:

|  | F X a | Plasmin |
|---|---|---|
| D-Phe—Pro—Arg—CH$_2$OH | 49% inhibition | 67% inhibition |
| 4-carboxyethylpheny ε-guanidinocaproate | 91% inhibition | 83% inhibition |

(plasmin substrate: D-norvalylcyclohexylalanylarginyl paranitroanilide (c=3 mmol/l)).

F Xa substrate: Bzl-Ile-Glu-Gly-Arg pNA (50% of the Glu as the methyl ester) (c=3 mmol/liter)

In the thrombin inhibition test (see above for the procedure), the substance Boc-D-Phe-Pro-Arg CH$_2$—OH showed an action which was about 1,000 times less than that of H-D-Phe-Pro-Arg CH$_2$—OH.

The inhibitory action on thrombin of H-D-Phe-Pro-argininol 4-nitrobenzoate dihydrochloride approximately corresponded to that of 4-carboxyethylphenyl ε-guanidinocaproate.

I claim:

1. An oligopeptidylargininol derivative and its homologs of the formula

X-D-Phe-Pro-A-Y.(HB)$_n$ being a hydrogen atom or a known protective group customary in peptide chemistry, D-Phe being D-phenylalanine, Pro being L-proline, A being an argininol residue or homologs of argininol of the general formula —NHCH[(CH$_2$)$_m$NHC(NH)NH$_2$]CH$_2$—O— m being 2 to 5;

Y being a hydrogen atom, a radical of the following structure:

Y=—OC—R, with R=H, an aliphatic radical having up to 4 carbon atoms, or

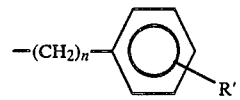

R' being H, CH$_3$, OCH$_3$ or NO$_2$, and n being 0, 1 or 2, or a radical of the following structure:

Y=—SO$_2$—R with R=OH, an aromatic or araliphatic radical of the structure

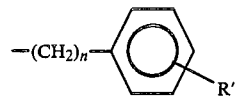

R' being H, CH$_3$ or OCH$_3$, and n being 0, 1 or 2,

B being an acid residue, and n being 0, 1 or 2.

2. A compound as claimed in claim 1 wherein m is 3 or 4.

3. A compound as claimed in claim 1, wherein A is an L-argininol or L-homoargininol residue.

4. D-phenylalanyl-L-prolyl-L-arininol and its physiologically tolerated salts.

5. A pharmaceutical agent which contains a pharmaceutically effective amount for inhibition of thrombin or as an anticoaqulent of a substance as claimed in claim 1, or its physiologically tolerated salt, and a physiologically acceptable vehicle.

6. A pharmaceutical agent containing a pharmaceutically effective amount for inhibition of thrombin or as an anticoagulant of D-phenylalanyl-L-prolyl-L- arginol or its physiologically tolerated salts.

7. A method for the treatment of a mammal in need of inhibitory action on thrombin which comprises administering to said mammal a pharmaceutically effective amount of a compound as claimed in claim 1 to inhibit formation of thrombin.

8. A method for the treatment of a mammal in need of an anticoagulent which comprises administering to said mammal a pharmaceutically effective amount of a compound as claimed in claim 1 to inhibit coagulation.

* * * * *

UNITED STATES PATENT AND TRADEMARK OFFICE
CERTIFICATE OF CORRECTION

PATENT NO. : 4,713,369

DATED : December 15, 1987

INVENTOR(S) : Werner Stüber

It is certified that error appears in the above-identified patent and that said Letters Patent is hereby corrected as shown below:

In Abstract, line 8, "guanidiano" should be --guanidino--.

Claim 4, column 10, line 33, "arininol" should be --argininol--.

Claim 5, column 10, line 37, "anticoaqulent" should be --anticoagulent--.

Signed and Sealed this

Nineteenth Day of July, 1988

Attest:

DONALD J. QUIGG

Attesting Officer

Commissioner of Patents and Trademarks